(12) United States Patent
Rao et al.

(10) Patent No.: US 9,309,499 B2
(45) Date of Patent: Apr. 12, 2016

(54) FUSION PROTEINS AND METHODS FOR TREATING HIV INFECTION AND AIDS RELATED SYMPTOMS

(75) Inventors: Pingfan Rao, Fuzhou (CN); Shutao Liu, Fuzhou (CN)

(73) Assignee: TIANJIN XIJI BIOTECHNOLOGY CO., LTD., Tianjin (CN)

(*) Notice: Subject to any disclaimer, the term of this patent is extended or adjusted under 35 U.S.C. 154(b) by 267 days.

(21) Appl. No.: 13/983,026

(22) PCT Filed: Feb. 1, 2011

(86) PCT No.: PCT/CN2011/070875
§ 371 (c)(1),
(2), (4) Date: Sep. 5, 2013

(87) PCT Pub. No.: WO2012/103684
PCT Pub. Date: Aug. 9, 2012

(65) Prior Publication Data
US 2013/0336946 A1 Dec. 19, 2013

(51) Int. Cl.
| | |
|---|---|
| A61K 38/44 | (2006.01) |
| A61K 45/06 | (2006.01) |
| A61K 47/48 | (2006.01) |
| B82Y 5/00 | (2011.01) |
| C12N 9/10 | (2006.01) |
| C12N 9/02 | (2006.01) |
| C07K 14/47 | (2006.01) |
| C07K 19/00 | (2006.01) |

(52) U.S. Cl.
CPC ............ *C12N 9/0089* (2013.01); *A61K 38/446* (2013.01); *A61K 45/06* (2013.01); *A61K 47/48361* (2013.01); *B82Y 5/00* (2013.01); *C07K 14/4711* (2013.01); *C12N 9/1088* (2013.01); *C12Y 115/01001* (2013.01); *C12Y 205/01018* (2013.01); *C07K 2319/036* (2013.01)

(58) Field of Classification Search
CPC ............... A61K 38/446; A61K 45/06; A61K 47/48361; B82Y 5/00; C07K 14/4711; C07K 2319/036; C12N 9/0089; C12N 9/1088; C12Y 115/01001; C12Y 205/01018
See application file for complete search history.

(56) References Cited

FOREIGN PATENT DOCUMENTS

| CN | 1301744 A | 7/2001 |
|---|---|---|
| WO | WO 2004/053136 A1 | 6/2004 |

OTHER PUBLICATIONS

Sadowski et al., Current Opinion in Structural Biology 19:357-362, 2009.*
Seffernick et al., J. Bacteriol. 183(8):2405-2410, 2001.*
Witkowski et al., Biochemistry 38:11643-11650, 1999.*
Åkerlund, B. et al., 1996: "Effect of N-acetylcysteine (NAC) treatment on HIV-1 infection: a double-blind placebo-controlled trial" *European Journal of Clinical Pharmacology* 50(6):457-461.
Aquaro, S. et al., 2008: "Oxidative stress and HIV infection: target pathways for novel therapies?" *Future HIV Therapy* 2(4):327-338.
Breitkreutz, R. et al., 2000: "Improvement of immune functions in HIV infection by sulfur supplementation: Two randomized trials" *Journal of Molecular Medicine* 78(1):55-62.
Flores, S.C. et al., 1993: "Tat protein of human immunodeficiency virus type 1 represses expression of manganese superoxide dismutase in HeLa cells" *Proceedings of the National Academy of Sciences* USA 90; 7632-7636.
Fridovich, I. 1983: "Superoxide Radical: An Endogenous Toxicant" *Annual Reviews Pharmacology Toxicology* 23: 239-257.
Hayakawa, M. et al., 1991: "Massive Conversion of Guanosine to 8-Hydroxy-Guanosine in Mouse Liver Mitochondrial DNA by Administration of Azidothymidine" *Biochemical Biophysical Research Communications* 176:87-93.
Jariwalla, R.J. et al., 2008: "Restoration of Blood Total Glutathione Status and Lymphocyte Function Following α-Lipoic Acid Supplementation in Patents with HIV Infection" *The Journal of Alternative and Complementary Medicine*, 14(2): 139-146.
Kwon, H.Y. et al., 2000 Transduction of Cu,Zn-superoxide mediated by an HIV-1 Tat protein basic domain into mammalian cells. *FEBS Letters* 485: 163-167.
Lewis, M. and Dalakas, M.C., 1995: "Mitochondrial toxicity of antiviral drugs" *Nature Medicine* 1:417-422.
Polyakov, V.M. et al., 1992: "Superoxide anion (O2-) production and enzymatic disbalance in peripheral blood cells isolated from HIV-infected children" *International Conference AIDS*, Amsterdam, Netherlands, Jul. 19-24; 8:32 (abstract No. PuA 6129).
Premanathan, M. et al., 1997: "Lecithinized Superoxide Dismutase: An Inhibitor of Human Immunodeficiency Virus Replication" *AIDS research and Human Retroviruses* 13(4): 283-291.
Wanchu, A. et al., 2009: "Short Communication: Oxidative Stress in HIV-Infected Individuals: A Cross-Sectional Study" *AIDS Research and Human Retroviruses* 25(12):1307-1311.
Wang, F.-P. et al., 2004: "Expression and Trans-membrane Activity of Human Cu, Zn-SOD-TAT PTD." *Pharmaceutical Biotechnology* 11(1): 11-15.
Winterbourn, C.C. 1993: "Superoxide as an Intracellular Radical Sink" *Free Radical Biology & Medicine* 14:85-90.
First Office Action issued in Chinese Patent Application No. 201180003299.0, mailed on May 29, 2014.
Second Office Action issued in Chinese Patent Application No. 201180003299.0, mailed on Feb. 9, 2015.
Third Office Action issued in Chinese Patent Application No. 201180003299.0, mailed on Jul. 30, 2015.

* cited by examiner

*Primary Examiner* — Delia Ramirez
(74) *Attorney, Agent, or Firm* — Knobbe, Martens, Olson & Bear, LLP (57) ABSTRACT

The present invention discloses pharmaceutical compositions and methods for using a fusion protein comprising a superoxide dismutase and a transit peptide. The present invention also discloses pharmaceutical compositions and methods for using the fusion protein in combination with other antiretroviral agents for treating patients with AIDS or HTV infection.

8 Claims, 3 Drawing Sheets

(SEQ ID NO. 03) YGRKKRRQRRR
(SEQ ID NO. 04) YGRKKKKQRR
(SEQ ID NO. 05) YGRKKR
(SEQ ID NO. 06) RKKRRQRRR
(SEQ ID NO. 07) RRRRRRRRR
(SEQ ID NO. 08) AAVALLPAVLLALLAP
(SEQ ID NO. 09) AVLLPVLLAAP
(SEQ ID NO. 10) VTVLALGALAGVGVG
(SEQ ID NO. 11) GALFLGFLGAAGSTMGA
(SEQ ID NO. 12) MGLGLHLLVLAAALQGAMGLGLHLLLAAALQGA
(SEQ ID NO. 13) WEAKLAKALAKALAKHLAKALAKALKACEA
(SEQ ID NO. 14) WEAALAEALAEALAEHLAEALAEALEALAA
(SEQ ID NO. 15) LARLLARLLARLLRALLRALLRAL
(SEQ ID NO. 16) KLLKLLLKLWKLLLKLLK
(SEQ ID NO. 17) RQIKIWFQRRMKKWK
(SEQ ID NO. 18) DAATATRGRSAASRPTERPRAPARSASRPRRPVE
(SEQ ID NO. 19) GWTLNSAGYLLGKINLKALAALAKKIL
(SEQ ID NO. 20) KETWWETWWTEWSQPKKKRKV

```
  1   SPILGYWKIK  GLVQPTRLLL  EYLEEKYEEH  LYERDEGDKW
 41   RNKKFELGLE  FPNLPYYIDG  DVKLTQSMAI  IRYIADKHNM
 81   LGGCPKERAE  ISMLEGAVLD  IRYGVSRIAY  SKDFETLKVD
121   FLSKLPEMLK  MFEDRLCHKT  YLNGDHVTHP  DFMLYDALDV
161   VLYMDPMCLD  AFPKLVCFKK  RIEAIPQIDK  YLKSSKYIAW
201   PLQGWQATFG  GGDHPPKSDL  VPRGSYGRKK  RRQRRRATKA
241   VCVLKGDPV   QGIINFEQKE  SNGPVKVWGS  IKGLTEGLHG
281   FHVHEFGDNT  AGCTSAGPHF  NPLSRKHGGP  KDEERHVGDL
321   GNVTADKDGV  ADVSIEDSVI  SLSGDHCIIG  RTLVVHEKAD
361   DLGKGGNEES  TKTGNAGSRL  ACGVIGIAQ
```

Fig. 3

```
  1   ATKAVCVLKG  DGPVQGIINF  EQKESNGPVK  VWGSIKGLTE
 41   GLHGFHVHEF  GDNTAGCTSA  GPHFNPLSRK  HGGPKDEERH
 81   VGDLGNVTAD  KDGVADVSIE  DSVISLSGDH  CIIGRTLVVH
121   EKADDLGKGG  NEESTKTGNA  GSRLACGVIG  IAQYGRKKR
```

Fig. 4

FUSION PROTEINS AND METHODS FOR TREATING HIV INFECTION AND AIDS RELATED SYMPTOMS

FIELD OF THE INVENTION

The present invention relates generally to protein transduction domain (PTD) and superoxide dismutase fusion proteins and their use in inhibition of viral infection, and in particular infection of mammalian cells by the Human Immunodeficiency Virus (HIV) and in reduction or prevention of depletion of CD4+T cells as well as in improvement of symptoms and signs, quality of life.

REFERENCE TO SEQUENCE LISTING

The present application is filed along with a Sequence Listing in electronic format. The Sequence Listing is provided as a file entitled 15915568_1, created Jul. 31, 2013, which is approximately 10.1 Kb in size. The information in the electronic format of the Sequence Listing is incorporated herein by reference in its entirety.

BACKGROUND OF THE INVENTION

While human immunodeficiency virus (HIV) infection, which results in AIDS, is a relatively new infection in the human population, it has quickly risen to the foremost health problem in the world. HIV/AIDS is now the leading cause of death in sub-Saharan Africa, and is the fourth biggest killer worldwide. While better treatment methods are now known to prolong the life of patients with HIV infection, there is still no cure.

The HIV infection of CD4+ cells leads to progressive loss of CD4+ cells, causing the incidence of opportunistic infections and even death. Although there are divergent views on the pathogenesis of AIDS, one of generally accepted views is that oxidative stress with excessive oxygen free radicals caused by viral infection can activate the immune system (immune activation), and lead to progressive CD4+ cell depletion (Wanchu et al., 2009, AIDS Research and Human Retroviruses 25(12):1307-1311; Polyakov et al., Int Conf AIDS, 1992 Jul. 19-24; 8: 32 (abstract no. PuA 6129)). Oxygen free radicals also reported to have relationship with HIV replication (Oxidative stress and HIV infection: target pathways for novel therapies? Future HIV Therapy, 2(4):327-338, 2008). Because superoxide dismutase (SOD) is the most important antioxidant enzyme which catalyzes the dismutation of superoxide anion free radical to generate less toxic hydrogen peroxide and oxygen, it has been used to treat various oxygen free radical-related diseases (Winterbourn, 1993, Free Radical Biology & Medicine, 14:85-90). Studies indicated that SOD gene expression was inhibited in HeLa cells which were infected with HIV tat gene, and reduced antioxidant enzyme defense leads to rapid depletion of plasma thiol (Flores et al., Proc. Natl. Acad. Sci. USA, 1993; 90; 7632-7636). It was found that lecithinized SOD (PC-SOD) inhibits human HIV types 1 and 2 in MT-4 cells (Premanathan, et al., AIDS research and human retroviruses, 13(4), 1997).

Modern anti-HIV drugs target several different stages of the HIV life cycle, and several of the enzymes that HIV requires to replicate and survive. Some of the commonly used anti-HIV drugs include nucleoside reverse transcriptase inhibitors such as ddI, AZT, d4T, 3TC and tenofovir; non-nucleoside reverse transcriptase inhibitors such as nevirapine, efavirenz and delavirdine; protease inhibitors such as saquinavir, amprenavir, lopinavir, ritonavir and indinavir. However, in many HIV infected patients, none of these antiviral drugs, alone or in combination, is effective to prevent the progression of chronic infection or treat acute AIDS. The high mutation rate of the HIV virus and associated emergence of HIV strains resistant to drugs is one large factor that results in the inability to effectively treat HIV infection. Further, the modern anti-HIV drugs are expensive. In addition, the majority of currently available antiviral drugs of HIV show mitochondrial toxicity (Lewis, 1995, Mitochondrial toxicity of antiviral drugs, Nature Med 1:417-422). For example, the mitochondrial toxicity of AZT (zidovudine) results from mutation in mitochondrial DNA caused oxygen free radicals (Hayakawa et al., Biochem Biophys Res Commun, 1991, 176:87-93).

Although oxygen free radicals were reported to be associated with HIV replication and the destruction of CD4+ T cells, several clinical trails with antioxidants indicated further trials were needed to determine whether they had a beneficial effect in the treatment of HIV-infected individuals (Effect of N-acetylcysteine (NAC) treatment on HIV-1 infection: a double-blind placebo-controlled trial, European Journal of Clinical Pharmacology, 50(6):457-461, 1996; Improvement of immune functions in HIV infection by sulfur supplementation: Two randomized trials, Journal of Molecular Medicine, 78(1):55-62, 2000; Restoration of Blood Total Glutathione Status and Lymphocyte Function Following α-Lipoic Acid Supplementation in Patients with HIV Infection, The Journal of Alternative and Complementary Medicine, 14(2): 139-146, 2008).

Accordingly, an inexpensive yet effective therapeutic and prophylactic treatment for HIV infection is desired. The treatment should be easily administered to those who are susceptible to or already have the virus. The present invention addresses these issues, as well as the problems presented in the prior art.

SUMMARY OF THE INVENTION

The present invention relates to discovery of compositions and methods of use of protein transduction domain (PTD) and superoxide dismutase (SOD) fusion proteins and optionally glutathione S-transferase (GST) as part of the fusion protein, and their use to inhibit viral infections in mammalian cells, and in particular human HIV infection. Specifically, the present invention relates to compositions comprising the fusion proteins and methods to use these compositions to inhibit the growth of HIV-1 infection in mammalian cells and patients.

Accordingly, in one aspect of the invention, a method for treating or inhibiting a Human Immunodeficiency Virus (HIV) infection, or treating or inhibiting Acquired Human Immunodeficiency Syndrome (AIDS), in a human patient is provided. The method involves administering a therapeutically effective amount of a fusion protein, or a or pharmaceutical composition thereof, which contains a superoxide dismutase (SOD) and a transit peptide. The carboxy terminus of the transit peptide is linked to the amino terminus of the SOD or vice versa, i.e., the amino terminus of the transit peptide is linked to the carboxy terminus of the SOD. The human patient treated with the fusion protein or pharmaceutical composition shows, as compared to the untreated human, a decrease in HIV RNA production and CD4+T cell depletion as well as improvement of symptoms and signs, quality of life. The SOD can be an SOD containing copper and zinc (Cu—Zn-SOD), SOD containing manganese (Mn-SOD) or an SOD containing iron (Fe-SOD). In one embodiment, SOD is Cu—Zn-SOD. The transit peptide used is one with a sequence of YGRKKRRQRRR (SEQ ID NO. 3), YGRKKKKQRR(SEQ ID NO. 4), YGRKKR (SEQ ID NO. 5), RKKRRQRRR (SEQ ID NO. 6), RRRRRRRRR (SEQ ID NO. 7) and other polyarginine (with 5-30 amino acid residues), AAVALLPAVLLALLAP (SEQ ID NO. 8), AVLLPVLLAAP (SEQ ID NO. 9), VTVLALGALAGVGVG (SEQ ID NO. 10), GALFLGFLGAAGSTMGA (SEQ ID NO. 11), MGLGLHLLVLAAALQGAMGLGLHLLLAAALQGA (SEQ ID NO. 12), WEAKLAKALAKALAKHLAKALAKALKACEA (SEQ ID NO. 13), WEAALAEALAEALAEHLAEALAEALEALAA (SEQ ID NO. 14), LARLLARLLARLLRALLRALLRAL (SEQ ID NO. 15), KLLKLLLKLWKLLLKLLK (SEQ ID NO. 16), RQIKIWFQRRMKKWK (SEQ ID NO. 17), DAATATRGRSAASRPTERPRAPARSASRPRRPVE (SEQ ID NO. 18), GWTLNSAGYLLGKINLKALAALAKKIL (SEQ ID NO. 19), KETWWETWWTEWSQPKKKRKV (SEQ ID NO. 20) or a polylysine (with 5-30 amino acid residues). The fusion protein can further include glutathione S-transferase (GST). In one embodiment, the carboxy terminus of the GST is linked to the amino terminus of the transit peptide. In a particularly preferred embodiment, the fusion protein is PS1 with an amino acid sequence as set forth in FIG. 3 or PS2 with an amino acid sequence as set forth in FIG. 4. The fusion protein or the pharmaceutical composition containing the fusion protein can be administered in pharmaceutically acceptable carrier by oral, buccal, sublingual, rectal or parenteral route.

In an embodiment, a therapeutically effective amount of at least one other antiretroviral agent(s), including pharmaceutically acceptable salts thereof, used for treatment of AIDS or HIV infection can be administered in addition to the fusion protein. The at least one other antiretroviral agent(s) can be nucleoside HIV reverse transcriptase inhibitors, non-nucleoside HIV reverse transcriptase inhibitors and HIV protease inhibitors. The dosage of the fusion protein can range from 0.01-10.00 MU (million unit of SOD activity), the preferable range being from 0.10-2.50 MU. The human patient may be resistant to antiretroviral therapy (ART) and yet will show a decrease in HIV RNA production and CD4+T cell depletion.

In another aspect of the invention, a pharmaceutical composition containing a glutathione S-transferase (GST), protein transduction domain (PTD) and superoxide dismutase (SOD) fusion protein or just PTD and SOD fusion protein is provided. the fusion protein can be in a pharmaceutically acceptable carrier. In one embodiment, the pharmaceutically acceptable carrier is appropriate for sublingual administration. A kit containing the pharmaceutical composition is also part of the invention herein. In a preferred embodiment, the kit contains either the fusion protein set forth in FIG. 3 or FIG. 4.

These and other aspects of the invention will be described in greater detail herein.

DETAILED DESCRIPTION OF THE INVENTION

The present invention relates generally to protein transduction domain (PTD) and superoxide dismutase (SOD) fusion proteins and their use in inhibition of viral infection, and in particular infection of mammalian cells by the Human Immunodeficiency Virus (HIV) and in reduction or prevention of depletion of CD4+T cells as well as in improvement of symptoms and signs, quality of life. This invention presents a class of fusion proteins for inhibiting/treating of HIV infection, such fusion proteins containing at least one full-length SOD and at least one PTD and optionally glutathione S-transferase (GST). PTD is a protein domain which facilitates the efficient protein transduction across cell membrane to transverse covalently linked proteins, DNA and other molecules into almost all of tissues and cells, even across blood-brain barrier with high transduction efficiency without damage to cells. The delivery of SOD enzyme across cell membrane can be successfully achieved by its fusion with PTD. It can efficiently remove the superoxide anion and thus the oxidative stress, protecting CD4+ cells from HIV and inhibiting HIV viral replication within the infected cells. These fusion proteins can effectively eliminate oxidative stress within both infected cells and cells subject to risks of infection to achieve therapeutic effects of reducing viral replication and raising CD4+ cell level.

Fusion proteins of the present invention (GST-PTD-SOD fusion protein and SOD-PTD fusion protein) can inhibit HIV infection, and can be useful for the treatment of HIV infection and the consequent pathological conditions such as AIDS. As shown in the examples section below, these fusion proteins are active on their own or in conjunction with a wide variety of other agents particularly those beneficial in HAART (highly active antiretroviral therapy) and other new combination compositions and therapies.

One skilled in the art would know that there are three distinct types of SOD depending on the metal cofactor in its reactive centre: SOD containing copper and zinc(Cu—Zn-SOD); SOD containing manganese (Mn-SOD) or iron (Fe-SOD). The SOD contemplated in the present invention can be any of these SODs. Further, for example, it can be Cu/Zn-SOD of human or bovine origin, can be recombinant, liposomal SODs as well as SODs of plant origin. Human Cu—Zn-SOD is preferred. Superoxide anions generally form when molecular oxygen acquires an additional electron, which happens when oxygen is subjected to ionizing radiation. Superoxide dismutases (SODs) catalyze the dismutation of superoxide into oxygen and hydrogen peroxide.

Determination of dismutase activity of SOD can be made spectrophotometrically at 505 nm, one unit of SOD is expressed as the amount of protein causing a 50% inhibition of formazan dye (505 nm), employing xanthine and xanthine oxidase to generate superoxide radicals, at 37° C. and at pH 7.8, based on the method described by Irvin Fridovich (Superoxide Radical: An Endogenous Toxicant, *Annual Review of Pharmacology and Toxicology*, Vol. 23: 239-257).

The present invention requires a PTD as part of fusion protein. PTD is a protein domain which facilitates the efficient protein transduction across cell membrane of covalently linked proteins (cargo proteins or peptides or SODs), DNA and other molecules into almost all of tissues and cells, even across blood-brain barrier with high transduction efficiency without damage to cells. The present invention relates to methods and materials for delivering a SOD across cells and tissues and even the blood-brain barrier into the brain. Delivery of SOD (cargo protein) according to this invention is accomplished by the use of a suitable PTD (transit peptide or transduction domain). The transit peptide allows for the transport of the C-terminus or N-terminus linked or fused cargo (SOD) into mammalian cells, tissues and/or across the blood brain barrier. In one embodiment of the invention, an SOD is linked to a YGRKKRRQRRR (SEQ ID NO. 3) transit peptide of the invention. In another embodiment, the cargo compound is linked to a YGRKKKKQRR (SEQ ID NO. 4) or YGRKKR (SEQ ID NO. 5) transport peptide of the invention. Other PTDs with amino acid sequences RKKRRQRRR (SEQ ID NO. 6), RRRRRRRRR (SEQ ID NO. 7), AAVALLPAVLLALLAP (SEQ ID NO. 8), AVLLPVLLAAP (SEQ ID NO. 9), VTVLALGALAGVGVG (SEQ ID NO. 10), GALFLGFLGAAGSTMGA (SEQ ID NO. 11), MGLGLHLLVLAAALQGAMGLGLHLLLAAALQGA (SEQ ID NO. 12), WEAKLAKALAKALAKHLAKALAKALKACEA (SEQ ID NO. 13), WEAALAEALAEALAEHLAEALAEALEALAA (SEQ ID NO. 14), LARLLARLLARLLRALLRALLRAL (SEQ ID NO. 15), KLLKLLLKLWKLLLKLLK (SEQ ID NO. 16), RQIKIWFQRRMKKWK (SEQ ID NO. 17), DAATATRGRSAASRPTERPRAPARSASRPRRPVE (SEQ ID NO. 18), GWTLNSAGYLLGKINLKALAALAKKIL (SEQ ID NO. 19), KETWWETWWTEWSQPKKKRKV (SEQ ID NO. 20) or a polylysine (with 5-30 amino acid residues), or a polyarginine (with 5-30 amino acid residues, e.g., RRRRRRRRR (SEQ ID NO. 7) can also be successfully used as PTD in place of YGRKKRRQRRR (SEQ ID NO. 3), YGRKKRRQRR (SEQ ID NO. 4) or YGRKKR (SEQ ID NO. 5). SOD may be linked to the C-terminus or N-terminus of the transit peptide. In some embodiments, a given transit peptide is linked at its N-terminus to glutathione S-transferase (GST). As used herein, the terms "linked," "complexed" or "fused" refer to the chemical association between protein or amino acid components being linked (as in GST-PTD-SOD fusion protein or SOD-PTD fusion protein). In some cases, the association may not be direct, but may be mediated by a linking group or another component. The chemical association between the components is by covalent bonds. The fusion site or linkage site may be made susceptible to enzymatic cleavage The PTD may be nature, chemically synthesized or prepared by recombinant technology. Such natural synthetic or recombinant transit domains may be used to transport linked cargo into mammalian cells, tissues and/or across the blood brain barrier. As used herein, the terms "polypeptide," "peptide," and "protein" are used interchangeably to refer to a polymer of amino acid residues. The terms apply to naturally occurring amino acid polymers. The terms also apply to amino acid polymers in which one or more amino acid residue is an artificial chemical analogue of a corresponding naturally occurring amino acid. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well. Specifically, these peptide sequences, which retain the inhibitory activity, can be prepared synthetically in accordance with well known methods such as solid or solution phase peptide synthesis. Alternatively, peptides of the present invention may be synthesized recombinantly.

For example, the fusion gene or nucleic acid sequence encoding GST-PTD-SOD fusion protein can be constructed by DNA recombinant technology and inserted into expression vector pGEX-2T. Suitable bacterial hosts such as E. coli (BL21, DH5a) are then transformed with the expression vector pGEX-2T containing the inserted GST-PTD-SOD. pGEX-2T cloning vector, complete sequence (GenBank: U13850.1) (both FASTA and graphics) (the sequence of which is incorporated herein by reference) can be obtained from the National Center for Biotechnology Information (NCBI), U.S. National Library of Medicine, 8600 Rockville Pike, Bethesda Md., 20894 USA. The GST-PTD-SOD fusion protein can be expressed in the E. coli by the induction IPTG and isolated by affinity chromatography for use in treating or inhibiting HIV infection/AIDS in a human patient.

The fusion gene or nucleic acid sequence encoding SOD-PTD can be constructed by PCR technology and inserted into the chromosome of the yeast of Pichia pastoris via a shuttle vector such as any of pPICZα A, B or C. Details of these vectors and vector sequences can be obtained from Invitrogen Corporation, 1600 Faraday Ave. Carlsbad, Calif. 92008. See also Invitrogen User Manual, entitled EasySelect™ Pichia Expression Kit For Expression of Recombinant Proteins Using pPICZ and pPICZα in Pichia pastoris, Cat. No. K1740-01, Jun. 18, 2010, Manual Part No. 25-0172. The vectors, pPICαA, B, and C, are 3.6 kb vectors used to express and secrete recombinant proteins in Pichia pastoris. Recombinant proteins are expressed as fusions to an N-terminal peptide encoding the Saccharomyces cerevisiae á-factor secretion signal. One skilled in the art would know that these vectors allow high-level, methanol inducible expression of the gene of interest in Pichia, and can be used in any Pichia strain including X-33, SMD 1168H, and KM71H. These vectors typically contain the following elements: AOX1 promoter for tightly regulated, methanol-induced expression of the gene of interest; α-factor secretion signal for directing secreted expression of the recombinant protein; Zeocin resistance gene for selection in both E. coli and Pichia; C-terminal peptide containing the c-myc epitope and a polyhistidine (6xHis) tag for detection and purification of a recombinant fusion protein. These commercially available vectors (A, B, C versions) are provided with reading frames to facilitate in-frame cloning with the C-terminal peptide. The fusion protein secreted by the host cell (yeast or E. coli) can be purified by filtration, alcohol precipitation and ion-exchange chromatography for use in treating or inhibiting HIV infection/AIDS in a human patient. "Patient" means a human infected with the HIV virus and in need of therapy as understood by practitioners in the field of AIDS and HIV infection.

The active agent consisting of GST, a PTD and SOD fusion protein or a PTD and SOD fusion protein or compositions containing the active agent may be administered to a human patient by any suitable route, for example, by oral, buccal, sublingual, rectal or parenteral (including intravenous, intramuscular, subcutaneous and intracoronary administration) route. Pharmaceutical compositions comprising the compositions of the present invention can be formulated in a conventional manner using one or more physiologically acceptable carriers or excipients or auxiliaries that facilitate processing of the composition, active agents or food additives, or a mixture thereof into preparations which can be used therapeutically. In various embodiments, the composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier can vary depending on the mode of administration.

The fusion proteins of the invention will generally be given as a pharmaceutical composition, and the active ingredient of the composition may be comprised of the fusion protein of the invention alone (i.e., GST-PTD-SOD or SOD-PTD alone) or the fusion protein and at least one other agent used for treating AIDS or HIV infection. The compositions will generally be made with a pharmaceutically accepted carrier or vehicle, and may contain conventional excipients. The compositions are made using common formulation techniques. The invention encompasses all conventional forms. Solid and liquid compositions are preferred. Some solid forms include powders, tablets, capsules, and lozenges. Tablets include chewable, buffered, and extended release. Capsules include enteric coated and extended release capsules. Powders are for both oral use and reconstitution into solution. Powders include lyophilized powders.

The compositions of the invention and pharmaceutical formulations thereof can be administered in any amount effective to achieve its intended purpose. When administrated to inhibit Human Immunodeficiency Virus (HIV) viral infection, treat AIDS and/or to reduce or prevent depletion of CD4+ T cells in a host or host cell, the composition is administered in a therapeutically effective amount. "Therapeutically effective amount" means the amount of agent required to provide a meaningful patient benefit—suppression of viral load, suppression of CD4+ T-cell depletion, restoration and preservation of immunologic function, improved quality of life, and/or reduction of HIV-related morbidity and mortality. Guidance for the dosage and administration schedule of various cargo compounds may be gathered from the many references which describe the use of such compounds in treatment or diagnosis, such as the Physicians' Desk Reference (PDR), or as otherwise determined by one of ordinary skill in the art.

The appropriate dosage may vary depending upon, for example, the human patient, the mode of administration and the nature and severity of the condition being treated or diagnosed. However, in one embodiment of the methods of the present invention, satisfactory treatment results in humans are indicated to be obtained at daily dosages from about 0.1 MU to about 2.5 MU (million unit of SOD activity) conveniently administered, for example, in daily doses, weekly doses, monthly doses, and/or continuous dosing. Daily doses can be in discrete dosages from 1 to 12 times per day or more. Alternatively, doses can be administered every other day, every third day, every fourth day, every fifth day, every sixth day, every week, and similarly in day increments up to 30 days or more. Dosing can be continuous, intermittent or a single dose, using any applicable dosing form, including tablet, saline, patches, i.v. administration and the like. More specifically, the composition is administered in a therapeutically effective amount. While the invention encompasses all conventional modes of administration as described above, oral, sublingual and rectal routes of administration are, preferred. The specific dosing regime, however, will be determined by a physician using sound medical judgment.

The invention also encompasses methods where a given fusion protein of the invention is given in combination therapy. That is, the given fusion protein can be used in conjunction with, but separately from, other antiretroviral agents useful in treating AIDS and HIV infection. "Combination," "coadministration," "concurrent," and similar terms referring to the administration of fusion protein of the invention with at least one other anti-HIV agent mean that the components (fusion proteins and other antiretroviral agents) are part of a combination antiretroviral therapy or highly active antiretroviral therapy (HAART). HAART is well known to one skilled in the art. It uses a combination of several antiretroviral drugs. The drugs inhibit the ability of the virus to multiply in the body, and they slow down the development of AIDS. HAART is defined as the use of three or more antiretroviral medications, one of which has to be a protease inhibitor or PI, an NNRTI or non-nucleoside reverse transcriptase inhibitor, one of the nucleoside or nucleotide reverse transcriptase inhibitors or NRTIs (such as abacavir or tenofovir), an integrase inhibitor (e.g., raltegravir), or an entry inhibitor (e.g., Maraviroc or enfuvirtide) (WIHS publications, 2008).

The fusion proteins of this invention used in conjunction with other antiretroviral agents or existing antiviral drugs is expected to effectively remove oxygen free radicals within the mitochondria, play a synergistic therapeutic effect. Some of these other antiretroviral agents include HIV nucleoside reverse transcriptase inhibitors, such as ddI, AZT, d4T, 3TC and tenofovir; HIV non-nucleoside reverse transcriptase inhibitors, such as nevirapine, efavirenz and delavirdine; HIV protease inhibitors, such as saquinavir; amprenavir, lopinavir, ritonavir and indinavir; HIV integrase inhibitor, such as raltegravir; HIV entry and fusion Inhibitors such as enfuvirtide and maraviroc. The invention, however, is not limited to these specific antiretroviral agents suitable for combination therapy. In these combination methods, GST-PTD-SOD or SOD-PTD will generally be given in a daily dose of protein with a SOD activity from 1000 U to 2,500,000 U in conjunction with other agents. These other antiretroviral agents generally will be present in a unit range similar to agents of that class used clinically or therapeutically. Typically, this is 0.25-1000 mg/unit. The specific dosing regime, however, will be determined by a physician using sound medical judgment.

In one embodiment of the invention, a method for treating or inhibiting a Human Immunodeficiency Virus (HIV) infection, or treating or inhibiting Acquired Human Immunodeficiency Syndrome (AIDS), in a human patient involves the use of a fusion protein. Specifically, a therapeutically effective amount of a fusion protein containing a superoxide dismutase (SOD) and at least one transit peptide with a sequence of YGRKKRRQRRR (SEQ ID NO. 3) is administered. The carboxy terminus of the transit peptide is linked to the amino terminus of the SOD or vice versa. Cu—Zn-SOD is preferred. The fusion protein may contain glutathione S-transferase (GST) linked to the amino terminus of the transit peptide. By administering the fusion protein, the human patient treated with the pharmaceutical composition shows, as compared to the untreated human, a decrease in HIV RNA HIV production and CD4+T cell depletion.

In other various embodiments of the present invention, the methods of the present invention may be used for diagnostic, prophylactic or research purposes or treatment ex vivo followed by return to the human patient in addition to the direct therapeutic procedures described above. In these embodiments, a fusion protein containing SOD is delivered into a cell in vitro, ex vivo or in vivo. For example, delivery may be achieved in vitro by adding a GST, PTD and SOD fusion protein or a PTD and SOD fusion protein to a cell culture, such as a biopsy. Alternatively, delivery may be achieved ex vivo by adding a given fusion protein to a sample removed from a patient, for example, blood, tissue, or bone marrow, and returning the treated sample to the patient.

WORKING EXAMPLES

The following working examples are provided to demonstrate preferred embodiments of the invention, but of course, should not be construed as in any way limiting the scope of the present invention. The examples below were carried out using conventional techniques that are well known and routine to those of skill in the art, except where otherwise described in detail. Further, it should be appreciated by those of skill in the art that the techniques disclosed in the examples represent techniques found by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

SOD Containing Fusion Proteins and their Activity

Fusion proteins with and without GST were made, expressed and assayed for its enzymatic or biological activity as follows:

Constructs preparation: The nucleic acid sequence encoding GST-PTD-SOD fusion protein was constructed by DNA recombinant technology and inserted into expression vector pGEX-2T (GenBank: U13850.1). The fusion gene of SOD-PTD was constructed by PCR technology and inserted into the chromosome of the yeast of *Pichia pastoris* via the shuttle vector pPICZα A.

Cell culture and transfections: *E. coli* (BL21, DH511) cells were transformed with the expression vector pGEX-2T containing the inserted GST-PTD-SOD. The expression vector pPICZα A with the insertion of SOD-PTD was transformed into *Pichia pastoris* (X-33).

GST-PTD-SOD fusion protein preparation: GST-PTD-SOD was expressed in the *E. coli* by the induction of IPTG and prepared by affinity chromatography to electrophoretically pure for use.

SOD-PTD fusion protein preparation: SOD-PTD was secreted by the yeast after induced by methanol; purified by filtration, alcohol precipitation and ion-exchange chromatography for use.

SOD assays:SOD activity was assayed spectrophotometrically at 505 nm. One unit was expressed as the amount of protein causing a 50% inhibition of formazan dye (at 505 nm), employing xanthine and xanthine oxidase to generate superoxide radicals, based on the method described by Irvin Fridovich (Superoxide Radical: An Endogenous Toxicant, *Annual Review of Pharmacology and Toxicology*, Vol. 23: 239-257). SOD is Cu/Zn superoxide dismutase with a Gene ID of 6647 and NCBI Reference Sequence of NP_000445.1. NCBI Reference (Protein_ID) for GST is AAA57089.1.

```
Amino acid sequence of GST-PTD-SOD (SEQ ID NO. 1):
SPILGYWKIKGLVQPTRLLLEYLEEKYEEHLYERDEGDKWRNKKFELGLE

FPNLPYYIDGDVKLTQSMAIIRYIADKHNMLGGCPKERAEISMLEGAVLD
```

```
IRYGVSRIAYSKDFETLKVDFLSKLPEMLKMFEDRLCHKTYLNGDHVTHP

DFMLYDALDVVLYMDPMCLDAFPKLVCFKKRIEAIPQIDKYLKSSKYIA

WPLQGWQATFGGGDHPPKSDLVPRGS-YGRKKRRQRRR-ATKAVCVLKGD

GPVQGIINFEQKESNGPVKVWGSIKGLTEGLHGFHVHEFGDNTAGCTSAG

PHFNPLSRKHGGPKDEERHVGDLGNVTADKDGVADVSIEDSVISLSGDHC

IIGRTLVVHEKADDLGKGGNEESTKTGNAGSRLACGVIGIAQ

Amino acid sequence of SOD-PTD (SEQ ID NO. 2):
ATKAVCVLKGDGPVQGIINFEQKESNGPVKVWGSIKGLTEGLHGFHVHEF

GDNTAGCTSAGPHFNPLSRKHGGPKDEERHVGDLGNVTADKDGVADVSIE

DSVISLSGDHCIIGRTLVVHEKADDLGKGGNEESTKTGNAGSRLACGVIG

IAQ-YGRKKR
```

Example 2

Figure 1:
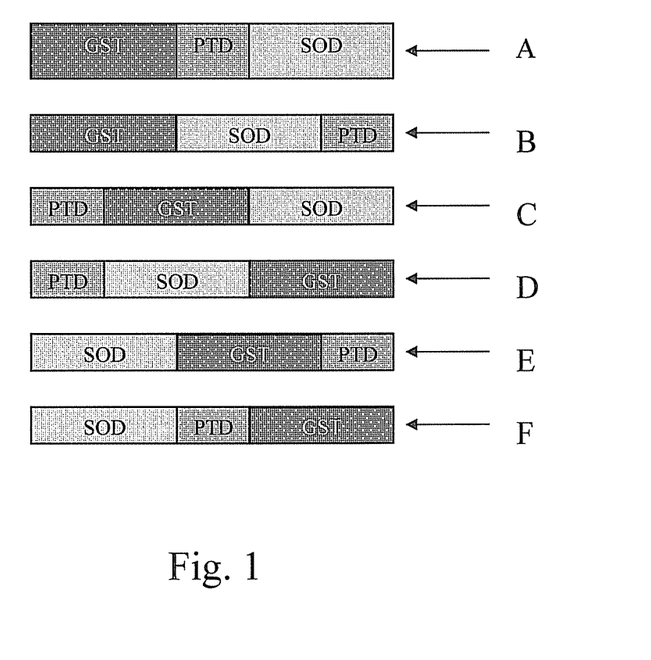
FIG. 1 shows schematics of various fusion proteins containing glutathione S-transferase (GST), protein transduction domain (PTD) and superoxide dismutase (SOD)
Figure 2:
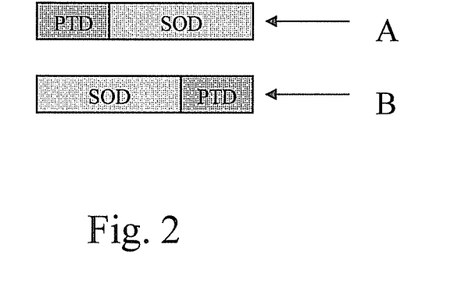
FIG. 2 shows schematics of various fusion proteins containing PTD and SOD
Figure 3:
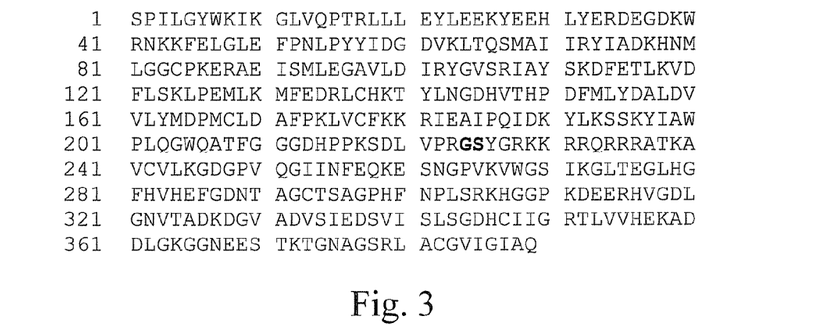
FIG. 3 shows amino acid sequence of GST-PTD-SOD fusion protein (SEQ ID NO. 1), referred to herein as PS1.
Figure 4:
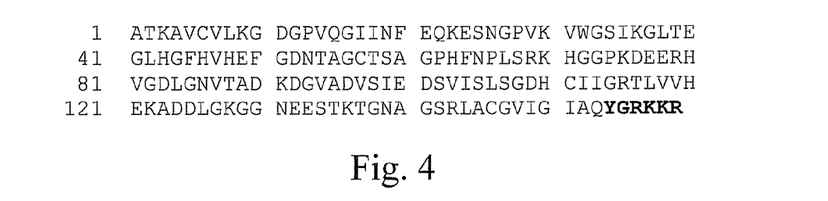
FIG. 4 shows amino acid sequence of SOD-PTD fusion protein (SEQ ID NO. 2), referred to herein as PS2.

Effect of Fusion Proteins PS1 and PS2 on HIV Viral Load and CD4+ T-Cell Count in HIV/AIDS Patients PS1 is a fusion protein consisting of glutathione S-transferase (GST), a PTD with a sequence of YGRKKRRQRRR (SEQ ID NO. 3) fused to the C-terminus of the GST, and Cu/Zn superoxide dismutase (SOD) fused to the C-terminus of the PTD as shown in FIG. 3. PS2 is a fusion protein consisting of a PTD with a sequence of YGRKKR (SEQ ID NO. 5) and Cu/Zn SOD fused to the N-terminus of the PTD as shown in FIG. 4. PS2 does not consist of glutathione S-transferase (GST). These fusion proteins are simply referred to herein as PS1 and PS2 and should be understood as such. Recombinant Cu/Zn SOD was made together with the two fusion proteins (PS1 and PS2) according the procedures described in Example 1.

Rectal Mucosa Administration of PSI/PS2

A total of 11 volunteer HIV/AIDS male patients were recruited. These patients were not subject to antiretroviral therapy (ART) or any other antiviral therapy for at least 3 months before the treatment of the present invention. Their HIV-RNA count was >50 cp/mL, not associated with other major infectious diseases (such as N1H1-influenza, tuberculosis, etc.). These volunteer patients signed the clinical trial consent after being well informed about PS1/PS2 by the attending doctor. They were randomly divided into four groups: (1) PS1 0.10 MU (million unit of SOD activity) group; (2) PS2 0.10 MU group; (3) PS2 0.50 MU group; and (4) PS2 2.50 MU group. Patients' basic information in each group is listed in Table 1-1. During the period of treatment, patients continued their work and normal life.

Pharmaceutical formulations, drug delivery, time, dose and duration: PS1 and PS2 freeze-dried powder with designated dosages (SOD activities) was dissolved into 2 ml saline and loaded to a 5-ml syringe with its needle removed. The syringe was inserted 5-10 cm into the rectum through the anus, and solution was injected. Patients would lie prone on bed for 10-30 min afterward. Each patient was administered PS1 or PS2 once every day before sleeping. The total treatment period was one month. Blood samples were collected before and at the end of the treatment for laboratory test. The laboratory analysis included CD4+ T-cell count and CD8+ T-cell count. CD8+ T cells kill HIV-infected cells, its count is associated with viral load and HIV RNA load, and liver function, renal function, full blood cell count, glycemia and so on.

Clinical drug safety: During treatment, each group of HIV/AIDS patients showed no vomiting, blurred vision, limb joint pain, muscle pain, numbness, paresthesia and any other adverse reactions, except 1 patient in PS2 2.50 MU group developed mild fever, which disappeared after appropriate rest. During the whole course of treatment, all patients maintained stable life symptoms, blood pressure, indicating sound clinical drug safety.

Changes in symptoms and signs: Compared with the medication before, each group of patients with one month treatment demonstrated a ruddy facial complexion, a significant increase mental, physical energy and sexual drive, and rash incidence dramatically decreased or stopped. No changes were observed in appetite, diarrhea, body weight.

CD4+ T-cell count and viral load changes: Patients' CD4+ T-cell count and viral load changes are shown in Table 1-2.

With one month of the administration of PS1, the patient's CD4+ was increased by 37.6/µL while the effect on the viral load decrease was modest. With one month of the administration of PS2, viral load was decreased with groups of lower dosages (0.10 MU and 0.50 MU), while maximum increase in CD4+ cell count was observed with 0.50 MU group. The high dosage group of 2.50 MU showed the least efficacy in both viral load reduction and CD4+ increase. Virus load changes of +0.19 for PS1 and −0.15 for PS2 2.50 MU are all within the error tolerance range since the detection method's 95% reliable error allowance is 0.3 Lg;

Rectal mucosa administration of PS1/PS2 had no discernable side effects on HIV/AIDS patients and can significantly improve symptoms and signs, improve their quality of life.

Sublingual Administration of PS1

A total of 10 volunteer HIV/AIDS patients were recruited. These patients were not subject to antiretroviral therapy (ART) or any other antiviral therapy for at least 3 months prior to the treatment described herein. These patients were paid blood donors infected with HIV in 1994-1996. Their HIV-RNA count was >50 cp/mL, not associated with other major infectious diseases (such as N1H1-influenza, tuberculosis, etc.). These volunteer patients signed the clinical trial consent after being well informed about PS1. They were randomly divided into two groups: treatment group and control group, patients' basic information in each group is listed in Table 1-3. During the period of treatment, all selected patients received centralized management but acted freely. The treatment began after a week of life to adapt to the environment.

Pharmaceutical formulations: Tablets were used in this experiment. The tablets for the treatment group contained food additives and 2,500 U/tablet of PS1, while the tablet for the control group contained food additives only. These tablets were manufactured in a food processing plant.

Drug delivery: Each patient was sublingually administered with PS1 tablets or control tablets.

Delivery time, dosage and duration: there times every day on AM 8:00, PM 2:00 and PM 8:00, each time 16 tablets. The total treatment period was 3 months.

Blood samples were collected pre-treatment and each one month post-treatment for laboratory test.

The laboratory analysis included CD4+ T-cell count and CD8+ T-cell count, HIV RNA load and liver function, renal function, full blood cell count, glycemia, and so on.

Clinical drug safety: During treatment, each group of HIV/AIDS patients showed no vomiting, blurred vision, limb joint pain, muscle pain, numbness, paresthesia and any other adverse reactions, except 1 patient in control group developed mild nausea once during the whole course of treatment. During medication, 3 patients in treatment group and 1 patient in control group developed fever associated with mild dizziness and headache; which disappeared after appropriate rest.

Patients showed no liver and kidney function deterioration after three months of sublingual administration of the tablets, and maintained stable life symptoms and blood pressure indicating sound clinical drug safety. Clinical symptoms and signs of patients before and after medication were shown in Table 1-4.

The patients in the treatment group with three-month medication showed ruddy facial complexion, and their mental, physical energy and male sexual drive were significantly increased, while hair loss was significantly decreased and 3 subjects grew new hair. Their body weight increased 4.34 Kg compared with 2.50 Kg of the control group; their rash incidence decreased or stopped, appetite, diarrhea did not change significantly. The patients in control group didn't show any improvement in their looking, mental and physical energy, hair loss, skin rash, diarrhea, appetite, male sexual function and other symptoms and signs.

CD4+ T-cell count and viral load changes: Patients' CD4+ T-cell count and viral load changes were shown in are shown in Table 1-5.

Sublingual administration of PS1 tablets for 3 months (three times daily, every time 16 tablets, each tablet of 2,500 U) demonstrated a good antiviral effect in HIV/AIDS patients. Compared with the control group, the viral load in the treatment group decreased by 1.08 LOG 10. The administration of PS1 also improved immune function. CD4+ T-cell count showed increase, but not as significantly.

Sublingual administration of PS1 showed no obvious side effects on HIV/AIDS patients and can significantly improve their complexion, mental and physical energy, hair, skin rashes, sexual function and other symptoms and signs, improve their quality of life.

Example 3

Effect of Fusion Protein PS1 on HIV Viral Load and CD4+ T-Cell Count in HIV/AIDS Patients Resistant to Antiretroviral Therapy (ART)

A total of 10 volunteers were recruited. They were paid blood donors infected with HIV in 1994-1996. These HIV/AIDS patients had regular treatment of ART for at least 3 months prior to the treatment described further herein. Their HIV-RNA count was >50 cp/mL, not associated with other major infectious diseases (such as N1H1-influenza, tuberculosis, etc.). These volunteer patients signed the clinical trial consent after being well informed about PS1. They were randomly divided into two groups: treatment group and control group, patients' basic information in each group is listed in Table 2-1. During the period of treatment, all selected patients received centralized management but acted freely. The treatment began after a week of life to adapt to the environment.

Pharmaceutical formulations: Tablets were used in this experiment. The tablets for the treatment group contained food additives and 2,500 U/tablet of PS1, the tablet for the control group contained food additives only, these tablets were manufactured in a food processing plant.

Drug delivery: Each patient was sublingually administered with PS1 tablets or control tablets. Delivery time, dosage and duration: There times every day at AM 8:00, PM 2:00 and PM 8:00, each time 16 tablets. The total treatment period was 3 months. Blood samples were collected pre-treatment and each one month post-treatment for laboratory test. The laboratory analysis included CD4+ T-cell count and CD8+ T-cell count, HIV RNA load and liver function, renal function, full blood cell count, glycemia, and so on.

Clinical drug safety: During the treatment, each group of HIV/AIDS patients showed no vomiting, blurred vision, limb joint pain, muscle pain, numbness, paresthesia and any other adverse reactions except the 2 patients in the treatment group and the 2 patient in the control group developed mild nausea once. During medication, 4 patients in the treatment group and 3 patients in the control group developed fever associated with mild dizziness and headache, which disappeared after appropriate rest.

During the whole course of medication, patients showed no liver and kidney function deterioration, kept with stable life symptoms, blood pressure, indicating a sound clinical drug safety. Changes in symptoms and signs: Clinical symptoms and signs of patients before and after medication were shown in Table 2-2.

Patients in treatment group demonstrated ruddy facial complexion, significant increase in mental, physical energy strength and sexual drive, and a significant decrease in hair loss with 2 subjects growing new hairs. Their body weight increased 3.33 Kg compared with 2.43 Kg of the control group; Appetite, rash, diarrhea did not change significantly. No significant changes were observed with the patients in the control group in their looking, spirit, physical strength, hair loss, skin rash, diarrhea, appetite, male sexual function and other symptoms and signs. CD4+ T-cell count and viral load changes: Patients' CD4+ T-cell count and viral load changes are shown in Table 2-3.

Sublingual administration of PS1 tablets (three times daily, every time 16 tablets, each tablet 2,500 U) demonstrated a remarkable antiviral effect in HIV/AIDS patients resistant to ART (also referred to herein as HIV/AIDS resistant patients). Compared with the control group, the viral load in the treated group decreased by 1.27 LOG 10, more than 1 LOG 10. The administration of PS1 also improved immune function with an increase of CD4+ T-cell count.

Sublingual administration of PS1 had no discernable side effects on HIV/AIDS patients and could significantly improve their complexion, mental, physical strength, hair, skin rashes, sexual function and other symptoms and signs, improve their quality of life.

Example 4

Effect of Rectal Administration of Fusion Protein PS2 in Combination with Highly Active Antiretroviral Therapies (HAART) on HIV Viral Load and CD4+ T-Cell Count in HIV/AIDS Patients A total of 3 volunteer HIV/AIDS male patients with treatment of HAART (AZT+3TC+EFV) for at least 3 months before this study were recruited. Their viral load was lower than detective level and not associated with other major infectious diseases (such as N1H1-influenza, tuberculosis, etc.). These volunteer patients signed the clinical trial consent after being well informed about PS2. They were randomly divided into 3 groups: PS2 0.10 MU (million unit of enzymatic activity) group, PS2 0.50 MU group, PS2 2.50 MU group. Patients' basic information in each group is listed in Table 3-1. During the period of treatment, patients continued their work and normal life.

Pharmaceutical formulations, drug delivery, time, dosage and duration: freeze-dried powder of PS2 of the corresponding dosage was dissolved into 2 ml saline and then loaded into a 5-ml syringe with the needle removed. The syringe was inserted 5-10 cm into the rectum through the anus, and the solution was injected. The patient lay prone on bed for 10-30 min afterwards. Each patient was administered PS2 once every day before sleeping. The total treatment period was one month. Blood samples were collected pre-treatment and post-treatment for laboratory test. The laboratory analysis included CD4+ T-cell count and CD8+ T-cell count, HIV RNA load and liver function, renal function, full blood cell count, glycemia, and so on.

Clinical drug safety: During treatment, each group of HIV/AIDS patients showed no vomiting, blurred vision, limb joint pain, muscle pain, numbness, paresthesia and other adverse reactions except 1 patient in PS2 2.50 MU group developed mild fever, which disappeared after appropriate rest; during whole course of treatment, all patients maintained stable life symptoms, blood pressure, indicating a sound clinical drug safety. Changes in symptoms and signs: each group of patients with one month treatment demonstrated ruddy complexion, significant improved in mental, physical strength significantly increased and appetite improved.

CD4+ T-cell count and viral load changes: Patients' CD4+ T-cell count change is shown in Table 3-2. Their viral load kept in LDL (lower detective level).

Within one month of the treatment, the administration of PS2 showed significant improvement in immune function. The CD4+ T-cell count increased by 81.7, an average increase of 31.6%. The effect in the cases of the dosage of 0.50 million and 2.50 million was better. Meanwhile, the administration of PS2 did not interfere with antiviral effect of HARRT. Rectal mucosa administration of PS2 combined with HARRT significantly improved symptoms and signs of HIV/AIDS patients and improve their quality of life.

TABLE 1-1

Basic information of clinical trial cases of HIV/AIDS

| Group | Case | Average age (years) | Average duration of HIV infetion (years) |
|---|---|---|---|
| PS1 0.10 MU | 2 | 23.50 ± 3.54 | 2.00 ± 1.41 |
| PS2 0.10 MU | 3 | 29.33 ± 1.15 | 2.33 ± 0.59 |
| PS2 0.50 MU | 3 | 30.67 ± 3.79 | 2.00 ± 1.00 |
| PS2 2.50 MU | 3 | 32.00 ± 7.00 | 1.67 ± 1.15 |

TABLE 1-2

The effect of rectal administration of PS1/PS2 on CD4+ T-cell count and viral load of HIV/AIDS Patients[a]

| Group | Average CD4 cell count (/μL) | | | Average viral load (Log10) | | |
|---|---|---|---|---|---|---|
| | Before | After | Change | Before | After | Change |
| PS1 0.10 MU | 376.0 | 413.6 | +37.6 | 4.41 | 4.60 | +0.19 |
| PS2 0.10 MU | 342.7 | 343.9 | +1.2 | 4.44 | 3.96 | −0.48 |
| PS2 0.50 MU | 644.7 | 679.4 | +34.7 | 3.95 | 3.51 | −0.44 |
| PS2 2.50 MU | 256.7 | 209.1 | −47.6 | 5.09 | 4.94 | −0.15 |

[a]CD4+ T-cell count and HIV RNA load: tested in National Centre for AIDS Prevention and Control (NCAIDS) of CDC, China. CD4+ T-cell count: Utilization of CD3/CD8/CD45/CD4 antibody, TruCOUNT tubes, FACS lysing solution, (BD Biosciences, San Jose, California, USA). HIV RNA load: NucliSens HIV-1 QT, NASBA, bioMe'rieux (Marcy L'Etoile, France).

TABLE 1-3

Basic information of clinical trial cases of HIV/AIDS

| Group | Case | Sex Male | Sex Female | Average age (years) | Average duration of HIV infection (years) |
|---|---|---|---|---|---|
| Treatment | 8 | 6 | 2 | 45.88 ± 3.40 | 13~15 |
| Control | 2 | 1 | 1 | 46.00 ± 1.6 | 13~15 |

TABLE 1-4

Clinical symptoms and signs of patients before and after medication

| Group | Before | After | Before | After | Before | After |
|---|---|---|---|---|---|---|
| | Complexion | | Spirit | | Physical strength | |
| Treatment | 1.38 ± 0.74 | 0.38 ± 0.52** | 0.75 ± 0.71 | 0** | 1.00 ± 0.76 | 0** |
| Control | 1.00 ± 0 | 1.00 ± 0 | 0 | 0 | 0 | 0 |
| | Appetite | | Hair | | Diarrhea | |
| Treatment | 0.50 ± 0.93 | 0.25 ± 0.46 | 1.13 ± 0.95 | 0* | 1.00 ± 0 | 0.63 ± 0.52 |
| Control | 0 | 0 | 0.50 ± 0.71 | 0.50 ± 0.71 | 1.00 ± 0 | 0.50 ± 0.71 |
| | Rash | | Sexual function (male) | | Weight | |
| Treatment | 0.25 ± 0.46 | 0 | 2.17 ± 0.75 | 0.50 ± 0.55** | 62.79 ± 9.04 | 67.13 ± 8.64 |
| Control | 0 | 0 | 0.50 ± 0.71 | 0.50 ± 0.71 | 80.00 ± 16.97 | 82.50 ± 17.68 |

Note:,
* and ** stand for significant difference with $P < 0.05$ and $P < 0.01$, respectively, when comparing the differences in the symptoms and signs of the same group before and after medication.

TABLE 1-5

The effect of sublingual administration of PS1 on CD4+ T-cell count and viral load of HIV/AIDS patients[a]

| Group | Viral load (Log10) Before | After one month | After two months | After three months | Change after three months | CD4+ T-cell count (/μL) Before | After one month | After two months | After three months | Change after three months |
|---|---|---|---|---|---|---|---|---|---|---|
| Treatment | 4.84 | 4.67 | 4.17 | 4.28 | −0.56 | 306 | 301 | 248 | 313 | 7 (2.3%) |
| Control | 5.05 | 5.22 | 5.21 | 5.57 | 0.52 | 281 | 313 | 323 | 353 | 72 (25.6%) |

TABLE 2-1

Basic information of clinical trial cases of HIV/AIDS resistant patients

| Group | Case | Sex Male | Sex Female | Average age (years) | Average duration of HIV infection (years) |
|---|---|---|---|---|---|
| Treatment | 6 | 4 | 2 | 51.50 ± 9.48 | 13~15 |
| Control | 4 | 3 | 1 | 50.75 ± 1.26 | 13~15 |

TABLE 2-2

Clinical symptoms and signs of patients before and after medication

| Group | Before | After | Before | After | Before | After |
|---|---|---|---|---|---|---|
| | Complexion | | Spirit | | Physical strength | |
| Treatment | 1.50 ± 0.55 | 0.33 ± 0.52** | 0.83 ± 0.41 | 0** | 1.33 ± 0.52 | 0.17 ± 0.41** |
| Control | 1.25 ± 0.50 | 1.25 ± 0.50 | 0.75 ± 0.96 | 0.50 ± 0.58 | 0.75 ± 0.96 | 0.75 ± 0.96 |
| | Appetite | | Hair | | Diarrhea | |
| Treatment | 0.33 ± 0.82 | 0.17 ± 0.41 | 0.83 ± 0.75 | 0* | 0.67 ± 0.52 | 0.67 ± 0.52 |
| Control | 0.25 ± 0.50 | 0.50 ± 1.00 | 0.75 ± 0.50 | 0.75 ± 0.50 | 0.75 ± 0.50 | 0.75 ± 0.50 |
| | Rash | | Sexual function (male) | | Weight | |
| Treatment | 0 | 0 | 2.75 ± 0.50 | 1.50 ± 1.01* | 64.42 ± 9.66 | 67.75 ± 9.36 |
| Control | 0 | 0.25 ± 0.50 | 2.33 ± 0.58 | 2.33 ± 0.58 | 58.95 ± 2.73 | 61.38 ± 2.87 |

Note:,
* and ** stand for significant difference With $P < 0.05$ and $P < 0.01$, respectively, when comparing the differences in the symptoms and signs of the same group before and after medication..

TABLE 2-3

The effect of sublingual administration of PS1 on CD4+ T-cell count and viral load of HIV/AIDS resistant patients[a]

| | Viral load (Log10) | | | | | CD4+ T-cell count (CD4/μL) | | | | |
|---|---|---|---|---|---|---|---|---|---|---|
| Group | Before | After one month | After two months | After three months | Change after three months | Before | After one month | After two months | After three months | Change after three months |
| Treatment | 4.02 | 3.80 | 3.93 | 3.59 | −0.43 | 358 | 283 | 294 | 366 | 8 (2.2%) |
| Control | 4.02 | 5.10 | 4.62 | 4.86 | 0.84 | 200 | 155 | 132 | 156 | −44 (−22.0%) |

TABLE 3-1

Basic information of clinical trial cases of HIV/AIDS

| Group | Case | Average age (years) | Duration of HIV infection (years) |
|---|---|---|---|
| PS2 0.10 MU | 1 | 45 | 9 |
| PS2 0.50 MU | 1 | 40 | 6 |
| PS2 2.50 MU | 1 | 30 | 4 |

TABLE 3-2

The effect of rectal mucosa administration of PS2 combined with HARRT on CD4+ T-cell count of HIV/AIDS patients[a]

| | CD4+ T-cell count (/μL) | | | |
|---|---|---|---|---|
| Group | Before | After | Change | Average Change |
| 0.10 MU | 250 | 310 | 60 (24.0%) | 81.7 (31.6%) |
| 0.50 MU | 340 | 458 | 118 (34.7%) | |
| 2.50 MU | 187 | 254 | 67 (35.8%) | |

[a]CD4+ T-cell count: tested in National Centre for AIDS Prevention and Control (NCAIDS) of CDC, China. CD4+ T-cell count: Utilization of CD3/CD8/CD45/CD4 antibody, Tru-COUNT tubes, FACS lysing solution, (BD Biosciences, San Jose, California, USA).

Thus, it has been demonstrated herein that the fusion proteins of the present invention are able to inhibit HIV activity and effective for treating HIV infected patients. The invention, however, should not be limited to the fusion proteins exemplified above. In fact, it may prove to be the case that the most useful pharmacological small molecule peptides and nucleic acids designed and synthesized in light of this disclosure will be second generation derivatives of the exemplified molecules.

All publications mentioned in the specification are indicative of the level of those skilled in the art to which this invention pertains. All publications, and patents and patent applications, if any, are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

What is claimed is:

1. A method for treating or inhibiting a Human Immunodeficiency Virus (HIV) infection, or treating or inhibiting Acquired Human Immunodeficiency Syndrome (AIDS) in a human patient, said method comprising administering to the human patient a therapeutically effective amount of a fusion protein or a pharmaceutical composition comprising said fusion protein, wherein said fusion protein comprises a superoxide dismutase (SOD) and a transit peptide, and wherein said fusion protein is the fusion protein of SEQ ID NO: 1.

2. The method of claim 1, wherein the fusion protein or the pharmaceutical composition is administered to the human patient in a pharmaceutically acceptable carrier by an oral, buccal, sublingual, rectal or parental route.

3. The method of claim 1 further comprising administering a therapeutically effective amount of at least one other anti-retroviral agent used for treatment of AIDS or HIV infection selected from the group consisting of a nucleoside HIV reverse transcriptase inhibitor, a non-nucleoside HIV reverse transcriptase inhibitor, and an HIV protease inhibitor, wherein the dosage range of the fusion protein is 0.01-10 MU (million units of SOD activity).

4. The method of claim 1, wherein said fusion protein or said pharmaceutical composition is administered to the human patient in a pharmaceutically acceptable carrier via a rectal mucosal route.

5. The method of claim 1, wherein said fusion protein of SEQ ID NO: 1 or said pharmaceutical composition is administered sublingually.

6. The method of claim 1, wherein said fusion protein of SEQ ID NO: 1 or said pharmaceutical composition is administered orally or sublingually.

7. The method of claim 1, wherein the human patient is resistant to antiretroviral therapy (ART).

8. The method of claim 1, wherein said fusion protein or said pharmaceutical composition is administered together with highly active antiretroviral therapy (HAART).

* * * * *

SEQUENCE LISTING

<160> NUMBER OF SEQ ID NOS: 20

<210> SEQ ID NO 1
<211> LENGTH: 389
<212> TYPE: PRT

<213> ORGANISM: Artificial sequence
<220> FEATURE:
<223> OTHER INFORMATION: Synthetic peptide

<400> SEQUENCE: 1

```
Ser Pro Ile Leu Gly Tyr Trp Lys Ile Lys Gly Leu Val Gln Pro Thr
1               5                   10                  15

Arg Leu Leu Leu Glu Tyr Leu Glu Glu Lys Tyr Glu Glu His Leu Tyr
            20                  25                  30

Glu Arg Asp Glu Gly Asp Lys Trp Arg Asn Lys Lys Phe Glu Leu Gly
        35                  40                  45

Leu Glu Phe Pro Asn Leu Pro Tyr Tyr Ile Asp Gly Asp Val Lys Leu
    50                  55                  60

Thr Gln Ser Met Ala Ile Ile Arg Tyr Ile Ala Asp Lys His Asn Met
65                  70                  75                  80

Leu Gly Gly Cys Pro Lys Glu Arg Ala Glu Ile Ser Met Leu Glu Gly
            85                  90                  95

Ala Val Leu Asp Ile Arg Tyr Gly Val Ser Arg Ile Ala Tyr Ser Lys
            100                 105                 110

Asp Phe Glu Thr Leu Lys Val Asp Phe Leu Ser Lys Leu Pro Glu Met
        115                 120                 125

Leu Lys Met Phe Glu Asp Arg Leu Cys His Lys Thr Tyr Leu Asn Gly
    130                 135                 140

Asp His Val Thr His Pro Asp Phe Met Leu Tyr Asp Ala Leu Asp Val
145                 150                 155                 160

Val Leu Tyr Met Asp Pro Met Cys Leu Asp Ala Phe Pro Lys Leu Val
                165                 170                 175

Cys Phe Lys Lys Arg Ile Glu Ala Ile Pro Gln Ile Asp Lys Tyr Leu
            180                 185                 190

Lys Ser Ser Lys Tyr Ile Ala Trp Pro Leu Gln Gly Trp Gln Ala Thr
        195                 200                 205

Phe Gly Gly Gly Asp His Pro Pro Lys Ser Asp Leu Val Pro Arg Gly
    210                 215                 220

Ser Tyr Gly Arg Lys Lys Arg Arg Gln Arg Arg Arg Ala Thr Lys Ala
225                 230                 235                 240

Val Cys Val Leu Lys Gly Asp Gly Pro Val Gln Gly Ile Ile Asn Phe
                245                 250                 255

Glu Gln Lys Glu Ser Asn Gly Pro Val Lys Val Trp Gly Ser Ile Lys
            260                 265                 270

Gly Leu Thr Glu Gly Leu His Gly Phe His Val His Glu Phe Gly Asp
        275                 280                 285

Asn Thr Ala Gly Cys Thr Ser Ala Gly Pro His Phe Asn Pro Leu Ser
    290                 295                 300

Arg Lys His Gly Gly Pro Lys Asp Glu Glu Arg His Val Gly Asp Leu
305                 310                 315                 320

Gly Asn Val Thr Ala Asp Lys Asp Gly Val Ala Asp Val Ser Ile Glu
                325                 330                 335

Asp Ser Val Ile Ser Leu Ser Gly Asp His Cys Ile Ile Gly Arg Thr
            340                 345                 350

Leu Val Val His Glu Lys Ala Asp Asp Leu Gly Lys Gly Gly Asn Glu
        355                 360                 365

Glu Ser Thr Lys Thr Gly Asn Ala Gly Ser Arg Leu Ala Cys Gly Val
    370                 375                 380

Ile Gly Ile Ala Gln
```

```
<210> SEQ ID NO 2
<211> LENGTH: 159
<212> TYPE: PRT
<213> ORGANISM: Artificial sequence
<220> FEATURE:
<223> OTHER INFORMATION: Synthetic peptide

<400> SEQUENCE: 2

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln Tyr Gly Arg Lys Lys Arg
145                 150                 155

<210> SEQ ID NO 3
<211> LENGTH: 11
<212> TYPE: PRT
<213> ORGANISM: Artificial sequence
<220> FEATURE:
<223> OTHER INFORMATION: Synthetic peptide

<400> SEQUENCE: 3

Tyr Gly Arg Lys Lys Arg Arg Gln Arg Arg Arg
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Tyr Gly Arg Lys Lys Lys Lys Gln Arg Arg
1               5                   10

<210> SEQ ID NO 5
<211> LENGTH: 6
<212> TYPE: PRT
<213> ORGANISM: Artificial sequence
<220> FEATURE:
<223> OTHER INFORMATION: Synthetic peptide

<400> SEQUENCE: 5

Tyr Gly Arg Lys Lys Arg
```

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Arg Lys Lys Arg Arg Gln Arg Arg Arg
1               5

<210> SEQ ID NO 7
<211> LENGTH: 19
<212> TYPE: PRT
<213> ORGANISM: Artificial sequence
<220> FEATURE:
<223> OTHER INFORMATION: Synthetic peptide

<400> SEQUENCE: 7

Ala Arg Thr Ile Phe Ile Cys Ile Ala Leu Arg Arg Arg Arg Arg
1               5                   10                  15

Arg Arg Arg

<210> SEQ ID NO 8
<211> LENGTH: 26
<212> TYPE: PRT
<213> ORGANISM: Artificial sequence
<220> FEATURE:
<223> OTHER INFORMATION: Synthetic peptide

<400> SEQUENCE: 8

Ala Arg Thr Ile Phe Ile Cys Ile Ala Leu Ala Ala Val Ala Leu Leu
1               5                   10                  15

Pro Ala Val Leu Leu Ala Leu Leu Ala Pro
            20                  25

<210> SEQ ID NO 9
<211> LENGTH: 11
<212> TYPE: PRT
<213> ORGANISM: Artificial sequence
<220> FEATURE:
<223> OTHER INFORMATION: Synthetic peptide

<400> SEQUENCE: 9

Ala Val Leu Leu Pro Val Leu Leu Ala Ala Pro
1               5                   10

<210> SEQ ID NO 10
<211> LENGTH: 15
<212> TYPE: PRT
<213> ORGANISM: Artificial sequence
<220> FEATURE:
<223> OTHER INFORMATION: Synthetic peptide

<400> SEQUENCE: 10

Val Thr Val Leu Ala Leu Gly Ala Leu Ala Gly Val Gly Val Gly
1               5                   10                  15

<210> SEQ ID NO 11
<211> LENGTH: 17
<212> TYPE: PRT
<213> ORGANISM: Artificial sequence
<220> FEATURE:
<223> OTHER INFORMATION: Synthetic peptide -continued

<400> SEQUENCE: 11

Gly Ala Leu Phe Leu Gly Phe Leu Gly Ala Ala Gly Ser Thr Met Gly
1               5                   10                  15

Ala

<210> SEQ ID NO 12
<211> LENGTH: 33
<212> TYPE: PRT
<213> ORGANISM: Artificial sequence
<220> FEATURE:
<223> OTHER INFORMATION: Synthetic peptide

<400> SEQUENCE: 12

Met Gly Leu Gly Leu His Leu Leu Val Leu Ala Ala Ala Leu Gln Gly
1               5                   10                  15

Ala Met Gly Leu Gly Leu His Leu Leu Leu Ala Ala Ala Leu Gln Gly
                20                  25                  30

Ala

<210> SEQ ID NO 13
<211> LENGTH: 30
<212> TYPE: PRT
<213> ORGANISM: Artificial sequence
<220> FEATURE:
<223> OTHER INFORMATION: Synthetic peptide

<400> SEQUENCE: 13

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
                20                  25                  30

<210> SEQ ID NO 14
<211> LENGTH: 30
<212> TYPE: PRT
<213> ORGANISM: Artificial sequence
<220> FEATURE:
<223> OTHER INFORMATION: Synthetic peptide

<400> SEQUENCE: 14

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
                20                  25                  30

<210> SEQ ID NO 15
<211> LENGTH: 24
<212> TYPE: PRT
<213> ORGANISM: Artificial sequence
<220> FEATURE:
<223> OTHER INFORMATION: Synthetic peptide

<400> SEQUENCE: 15

Leu Ala Arg Leu Leu Ala Arg Leu Leu Ala Arg Leu Leu Arg Ala Leu
1               5                   10                  15

Leu Arg Ala Leu Leu Arg Ala Leu
                20

<210> SEQ ID NO 16
<211> LENGTH: 18
<212> TYPE: PRT
<213> ORGANISM: Artificial sequence

```
<220> FEATURE:
<223> OTHER INFORMATION: Synthetic peptide

<400> SEQUENCE: 16

Lys Leu Leu Lys Leu Leu Leu Lys Leu Trp Lys Leu Leu Leu Lys Leu
1               5                   10                  15

Leu Lys

<210> SEQ ID NO 17
<211> LENGTH: 15
<212> TYPE: PRT
<213> ORGANISM: Artificial sequence
<220> FEATURE:
<223> OTHER INFORMATION: Synthetic peptide

<400> SEQUENCE: 17

Arg Gln Ile Lys Ile Trp Phe Gln Arg Arg Met Lys Lys Trp Lys
1               5                   10                  15

<210> SEQ ID NO 18
<211> LENGTH: 34
<212> TYPE: PRT
<213> ORGANISM: Artificial sequence
<220> FEATURE:
<223> OTHER INFORMATION: Synthetic peptide

<400> SEQUENCE: 18

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 19
<211> LENGTH: 27
<212> TYPE: PRT
<213> ORGANISM: Artificial sequence
<220> FEATURE:
<223> OTHER INFORMATION: Synthetic peptide

<400> SEQUENCE: 19

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 20
<211> LENGTH: 21
<212> TYPE: PRT
<213> ORGANISM: Artificial sequence
<220> FEATURE:
<223> OTHER INFORMATION: Synthetic peptide

<400> SEQUENCE: 20

Lys Glu Thr Trp Trp Glu Thr Trp Trp Thr Glu Trp Ser Gln Pro Lys
1               5                   10                  15

Lys Lys Arg Lys Val
            20
```